(12) United States Patent  (10) Patent No.: US 8,379,965 B2
Iwanaga  (45) Date of Patent: Feb. 19, 2013

(54) DEFECT CLASSIFICATION METHOD, COMPUTER STORAGE MEDIUM, AND DEFECT CLASSIFICATION APPARATUS

(75) Inventor: Shuji Iwanaga, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 339 days.

(21) Appl. No.: 12/736,204

(22) PCT Filed: Mar. 11, 2009

(86) PCT No.: PCT/JP2009/054646
§ 371 (c)(1),
(2), (4) Date: Sep. 20, 2010

(87) PCT Pub. No.: WO2009/119314
PCT Pub. Date: Oct. 1, 2009

(65) Prior Publication Data
US 2011/0007961 A1  Jan. 13, 2011

(30) Foreign Application Priority Data
Mar. 27, 2008  (JP) .................................. 2008-082740

(51) Int. Cl.
*G06K 9/00* (2006.01)
*G06K 9/62* (2006.01)
(52) U.S. Cl. ........................................ 382/149; 382/224
(58) Field of Classification Search .................. 382/149, 382/159, 224; 348/92
See application file for complete search history.

(56) References Cited

U.S. PATENT DOCUMENTS

| 6,092,059 A * | 7/2000 | Straforini et al. ................ 706/14 |
| 7,873,205 B2 * | 1/2011 | Okuda et al. ................... 382/145 |
| 2002/0168099 A1 | 11/2002 | Noy |
| 2005/0058335 A1 * | 3/2005 | Lin et al. ........................ 382/141 |

FOREIGN PATENT DOCUMENTS

| JP | A-2003-168114 | 6/2003 |
| JP | A-2004-077165 | 3/2004 |
| JP | A-2004-294360 | 10/2004 |
| JP | A-2005-274285 | 10/2005 |
| JP | A-2007-240519 | 9/2007 |
| TW | 577995 | 3/2004 |

* cited by examiner

*Primary Examiner* — Daniel Mariam
(74) *Attorney, Agent, or Firm* — Posz Law Group, PLC

(57) ABSTRACT

A defect classification apparatus of the present invention includes a design unit and a diagnosis unit. In the design unit, a model creation unit combines a defect template in a template storage unit with a teaching image to create a defect model, and a classification class setting unit calculates feature amounts of a defect in the defect model and sets a classification class of the defect. The relation between the feature amounts of the defect and the classification class is stored in a storage unit. In the diagnosis unit, a feature amount calculation unit calculates feature amounts of defects from a captured inspection object image of the substrate, and a classification unit classifies the defects of the substrate into classification classes from the relations between the feature amounts of the defects and the classification classes in the storage unit based on the calculated feature amounts of the defects.

17 Claims, 13 Drawing Sheets

(a)  (b)  (c)  (d)

(a)

(b)

(a)

| No. | Tag | ... | FEATURE AMOUNT 1 | FEATURE AMOUNT 2 | FEATURE AMOUNT 3 | FEATURE AMOUNT 4 | FEATURE AMOUNT5 | ... | CLASSIFICATION RESULT |
|---|---|---|---|---|---|---|---|---|---|
| 1 | AAA | ... | 8 | 7 | 11 | 5 | 10 | ... | 0 |
| ... | ... | ... | ... | ... | ... | ... | ... | ... | — |
| 8 | ... | ... | 38 | 47 | 17 | 66 | 76 | | 1 |
| ... | ... | ... | ... | ... | ... | ... | ... | ... | — |
| 18 | ... | ... | 32 | 59 | 16 | 59 | 137 | | 2 |
| ... | ... | ... | ... | ... | ... | ... | ... | ... | — |
| 26 | ... | ... | 42 | 53 | 12 | 51 | 106 | ... | 2 |

(b)

(a)

(b)

(c)

(d)

ively classify the defects. However, to optimally classify defects by the conventional learning-type classification, a large number of defect images need to be collected in advance. Therefore, at the startup of productive process, defects cannot be properly classified because of lack of the defect images. Further, when defects are classified using a small number of defect images, an over-matching phenomenon of learning to the defect images, called over-learning, occurs and it is difficult to properly classify the defects.

DEFECT CLASSIFICATION METHOD, COMPUTER STORAGE MEDIUM, AND DEFECT CLASSIFICATION APPARATUS

TECHNICAL FIELD

The present invention relates to a method of classifying defects of a substrate based on a captured image of the substrate, a computer storage medium, and a defect classification apparatus.

BACKGROUND ART

For example, in a photolithography process in manufacture of a semiconductor device, resist coating treatment for forming a resist film by applying a resist solution on, for example, a semiconductor wafer (hereinafter, referred to as a "wafer"), exposure processing for exposing the resist film to a predetermined pattern, developing treatment for developing the exposed resist film and so on are sequentially performed, whereby a predetermined resist pattern is formed on the wafer.

The wafer for which a series of photolithography process has been performed is subjected to a so-called macro defect inspection by an inspection apparatus to inspect whether or not a predetermined resist film is formed on the front surface of the wafer, or whether or not appropriate exposure processing has been performed, and whether or not there is a scratch or adherence of foreign substance.

Such macro defect inspection is performed such that while a mounting table mounting the wafer thereon is moved, illumination is applied to the wafer on the mounting table and an image of the wafer is captured by an imaging device, such as a CCD line sensor, and the image is subjected to image processing for judgment of presence or absence of a defect (Patent Document 1).

When judging the presence or absence of a defect, a method called a learning-type classification has been conventionally used to classify defects. In the learning-type classification, defect images are collected in advance as teaching images and learned, whereby defects can be optimally classified.

[Patent Document 1] Japanese Patent Application Laid-open No. 2007-240519

DISCLOSURE OF THE INVENTION

Problems to Be Solved by the Invention

However, to optimally classify defects by the conventional learning-type classification, a large number of defect images need to be collected in advance. Therefore, at the startup of productive process, defects cannot be properly classified because of lack of the defect images. Further, when defects are classified using a small number of defect images, an over-matching phenomenon of learning to the defect images, called over-learning, occurs and it is difficult to properly classify the defects.

The present invention is made in view of such points, and it is an object to properly classify defects of a substrate from a captured inspection object image of the substrate even when there is no defect image or when there are a small number of defect images.

Means for Solving the Problems

To attain the above object, the present invention is a defect classification method of classifying defects of a substrate based on a captured inspection object image of the substrate, including: a design step of setting classification classes of defects based on feature amounts of the defects and storing relations between the feature amounts of the defects and the classification classes into a storage unit; a feature amount calculation step of calculating the feature amounts of the defects of the substrate from the captured inspection object image of the substrate; and a classification step of classifying the defects of the substrate into the classification classes from the relations between the feature amounts of the defects and the classification classes stored in the storage unit based on the calculated feature amounts of the defects, the design step including: a first step of creating a plurality of defect templates; a second step of combining a teaching image of a substrate without defect with the defect template to create a defect model; a third step of calculating feature amounts of a defect in the defect model; a fourth step of setting a classification class of the defect with respect to the feature amounts of the defect in the defect model; and a fifth step of storing a relation between the feature amounts of the defect and the classification class into the storage unit.

According to the present invention, detect templates are created in advance, and the defect templates and the teaching image without defect are combined to create defect models, so that the defect models can be used as defect images in the conventional learning-type classification method. Then, a classification class of the defect can be set with respect to the feature amounts of the defect in the defect model, and a relation between the feature amounts of the defect and the classification class can be stored into the storage unit. Accordingly, even when there is no defect image or there are a small number of defect images, defects of the substrate can be properly classified by calculating feature amounts of defects from a captured inspection object image of the substrate and using the relations between the feature amounts of the defects and the classification classes of the defects stored in the storage unit.

In the design step, the feature amounts of the defects and the classification classes in the storage unit may be linked to information inherent in the substrate. Note that the information inherent in the substrate includes, for example, the ID of the substrate, the lot ID of the substrate, the processing conditions of the substrate, the processing date and time of the substrate and so on.

The present invention according to another aspect is a computer-readable storage medium storing a program running on a computer of a defect classification apparatus to cause the defect classification apparatus to execute the defect classification method.

The present invention according to still another aspect is a defect classification apparatus for classifying defects of a substrate based on a captured inspection object image of the substrate, including: a design unit for setting classification classes of defects based on feature amounts of the defects; and a diagnosis unit for classifying the defects of the substrate into the classification classes set by the design unit from the captured inspection object image of the substrate, the design unit including: a template storage unit storing a plurality of defect templates; a model creation unit for combining a teaching image of a substrate without defect with the defect template to create a defect model; a classification class setting unit for calculating feature amounts of a defect in the defect model and setting a classification class of the defect with respect to the feature amounts of the defect; and a storage unit for storing a relation between the feature amounts of the defect and the classification class, the diagnosis unit including: a feature amount calculation unit for calculating the feature amounts of the defects of the substrate from the captured inspection object image of the substrate; and a classification unit for classifying the defects of the substrate into the classification classes from the relations between the feature amounts of the defects and the classification classes stored in the storage unit based on the calculated feature amounts of the defects.

Effect of the Invention

According to the present invention, defects of a substrate can be properly classified from a captured inspection object image of the substrate even when there is no defect image or when there are a small number of defect images.

Figure 1:
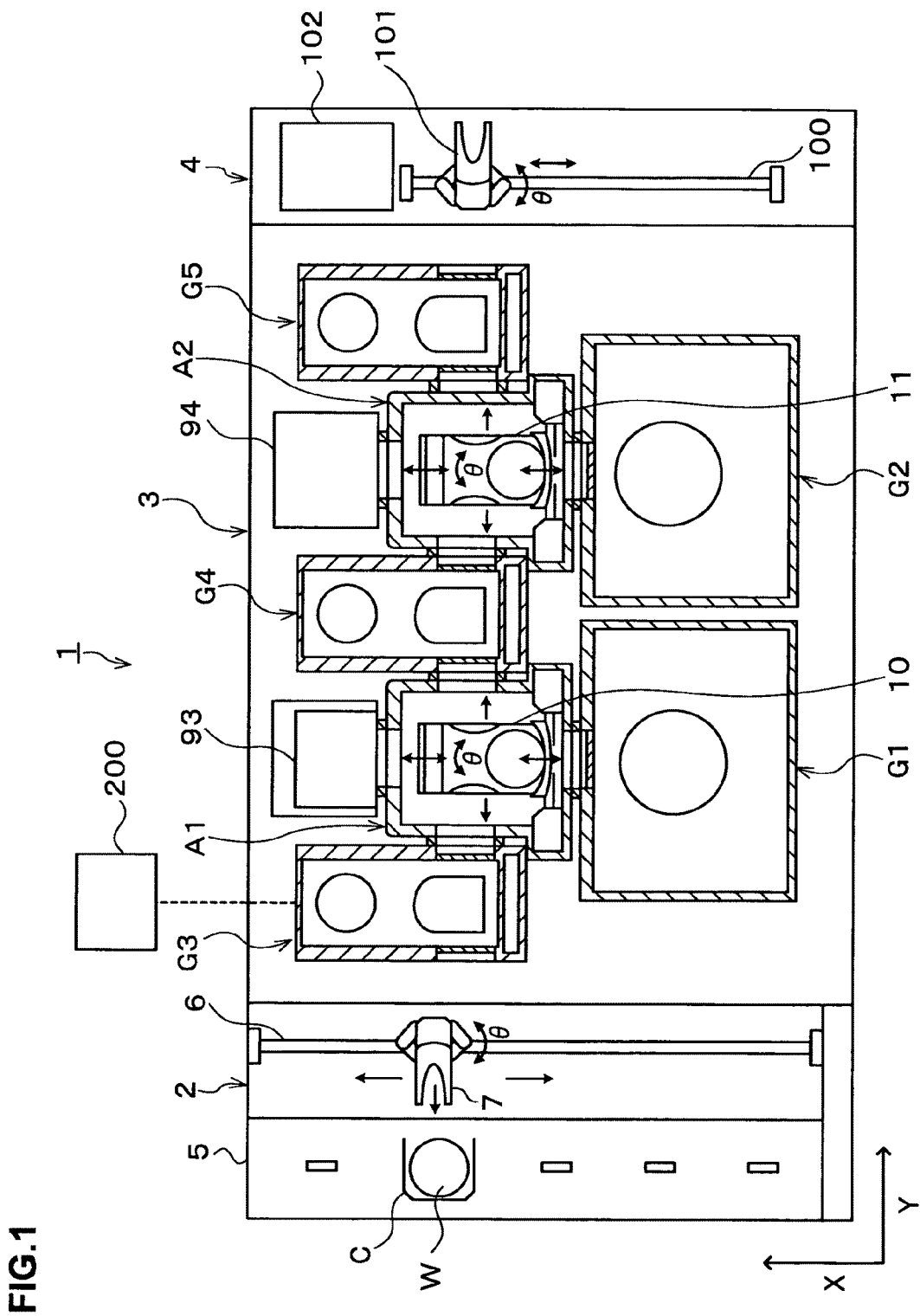
FIG. 1 A plan view schematically showing a configuration of a coating and developing treatment system including a defect classification apparatus according to this embodiment.

EXPLANATION OF CODES 1 coating and developing treatment system
110 defect inspection apparatus
200 defect classification apparatus
201 design unit
202 diagnosis unit
210 teaching image input unit
211 pre-design processing unit
212 template storage unit
213 model creation unit
214 first classification class setting unit
215 second classification class setting unit
220 storage unit
221 storage unit history management function
222 storage unit check function
223 learning and training unit
224 classification class correction unit
230 inspection object image input unit
231 pre-processing unit
232 feature amount calculation unit
233 classification unit
234 post-processing unit
235 confirmation unit
236 report unit
C chip
D defect
E inspection object image
M defect model
N1 teaching image without defect
N2 teaching image without defect
T defect template
W wafer

BEST MODE FOR CARRYING OUT THE INVENTION

Figure 2:
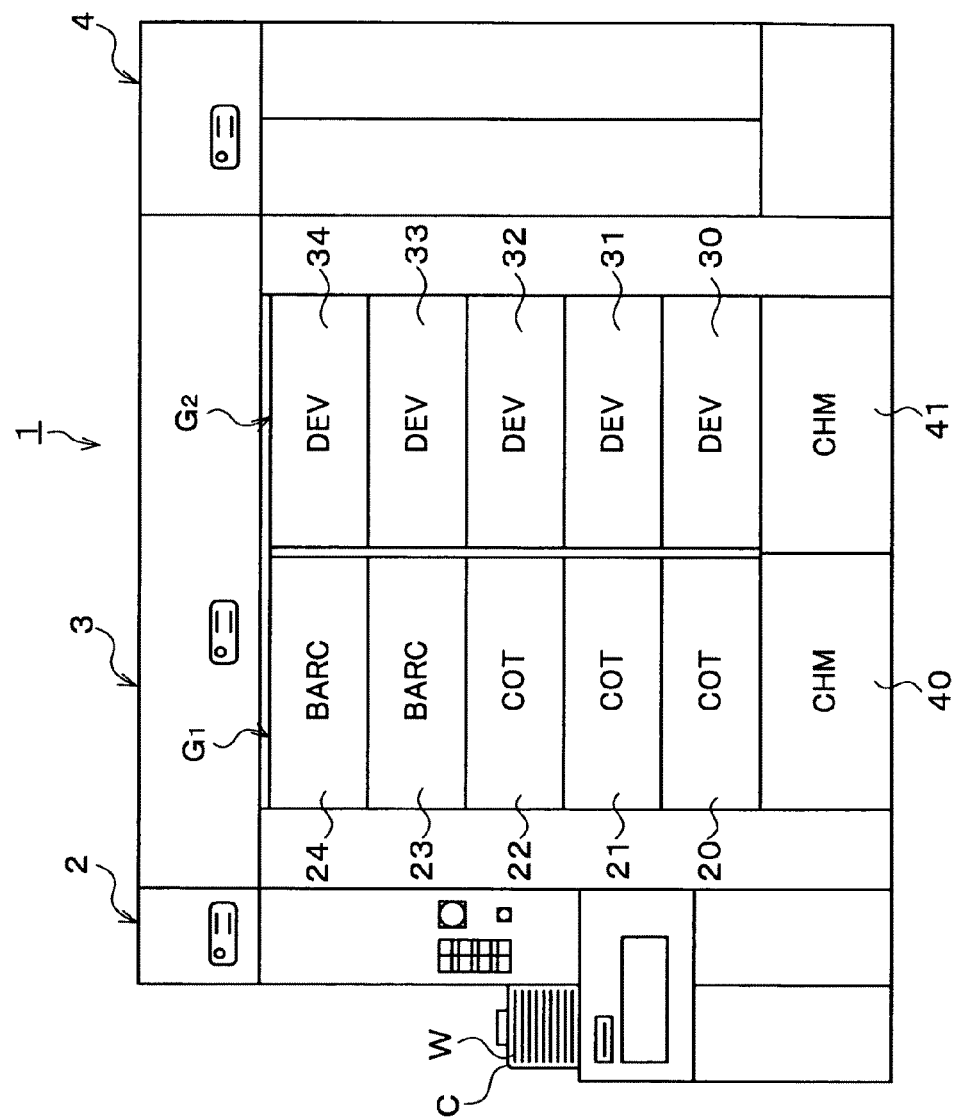
FIG. 2 A front view of the coating and developing treatment system.
Figure 3:
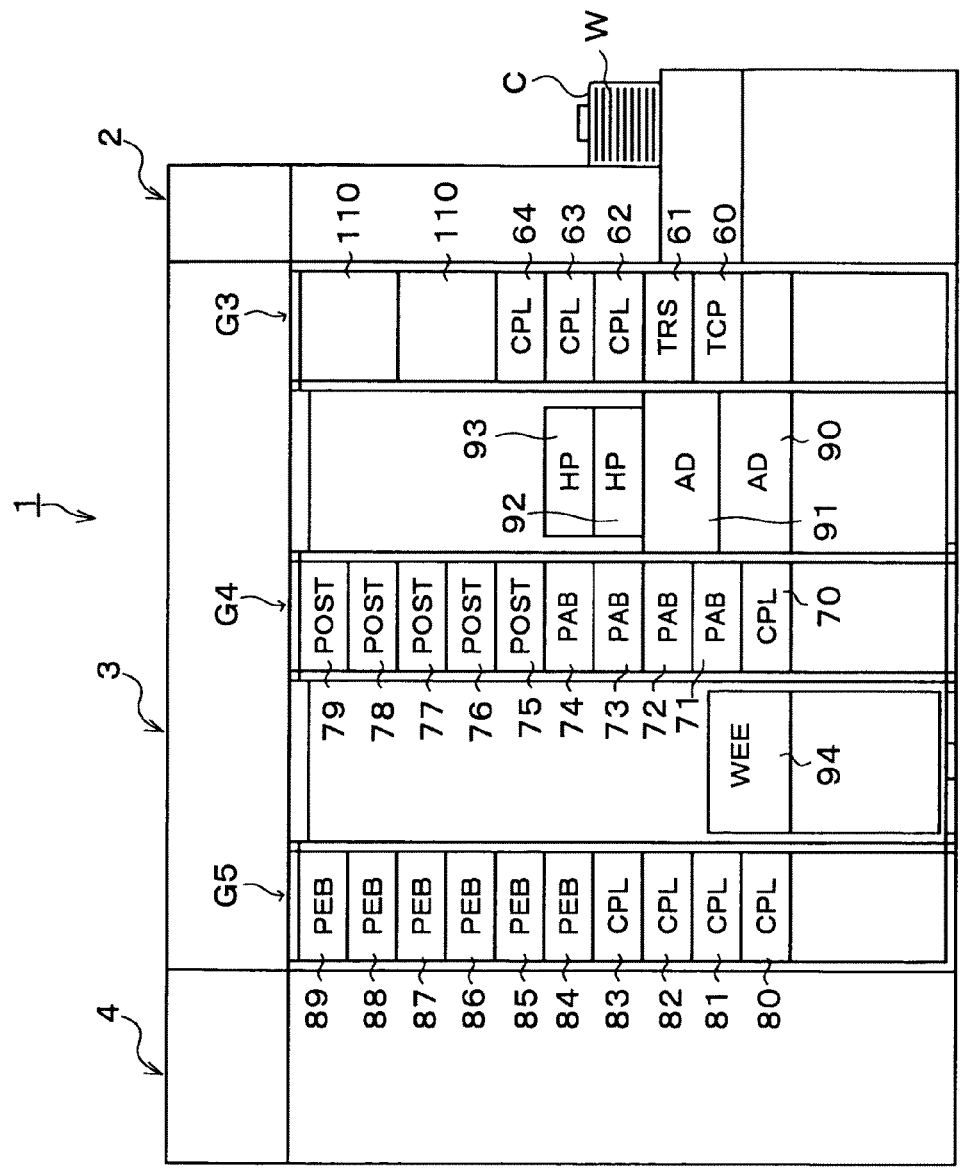
FIG. 3 A rear view of the coating and developing treatment system.

Hereinafter, a preferred embodiment of the present invention will be described. FIG. 1 is a plan view schematically showing a configuration of a coating and developing treatment system 1 including a defect classification apparatus according to this embodiment. FIG. 2 is a front view of the coating and developing treatment system 1, and FIG. 3 is a rear view of the coating and developing treatment system 1.

The coating and developing treatment system 1 has, as shown in FIG. 1, a configuration in which, for example, a cassette station 2 for transferring, for example, 25 wafers W per cassette as a unit from/to the outside into/from the coating and developing treatment system 1 and transferring the wafers W into/out of a cassette C; a processing station 3 including a plurality of various kinds of processing and treatment units, which are multi-tiered, for performing predetermined processing or treatment in a manner of single wafer processing in a photolithography process; and an interface station 4 for passing the wafer W to/from an aligner (not shown) provided adjacent to the processing station 3, are integrally connected.

In the cassette station 2, a cassette mounting table 5 is provided and configured such that a plurality of cassettes C can be mounted on the cassette mounting table 5 in a line in an X-direction (a top-to-bottom direction in FIG. 1). In the cassette station 2, a wafer transfer body 7 is provided which is movable in the X-direction on a transfer path 6. The wafer transfer body 7 is also movable in a wafer-arrangement direction of the wafers W housed in the cassette C (a Z-direction; the vertical direction), and thus can selectively access the wafers W in each of the cassettes C arranged in the X-direction.

The wafer transfer body 7 is rotatable in a θ-direction around the Z-axis, and can access a temperature regulating unit 60 and a transition unit 61 for passing the wafer W which are included in a later-described third processing unit group G3 on the processing station 3 side.

The processing station 3 adjacent to the cassette station 2 includes, for example, five processing unit groups G1 to G5 in each of which a plurality of processing and treatment units are multi-tiered. On an X-direction negative direction (downward direction in FIG. 1) side in the processing station 3, the first processing unit group G1 and the second processing unit group G2 are placed in order from the cassette station 2 side. On an X-direction positive direction (upward direction in FIG. 1) side in the processing station 3, the third processing unit group G3, the fourth processing unit group G4, and the fifth processing unit group G5 are placed in order from the cassette station 2 side. Between the third processing unit group G3 and the fourth processing unit group G4, a first transfer unit A1 is provided, and a first transfer arm 10 for supporting and transferring the wafer W is provided in the first transfer unit A1. The first transfer arm 10 can selectively access the processing and treatment units in the first processing unit group G1, the third processing unit group G3, and the fourth processing unit group G4 and transfer the wafer W to them. Between the fourth processing unit group G4 and the fifth processing unit group G5, a second transfer unit A2 is provided, and a second transfer arm 11 for supporting and transferring the wafer W is provided in the second transfer unit A2. The second transfer arm 11 can selectively access the processing and treatment units in the second processing unit group G2, the fourth processing unit group G4, and the fifth processing unit group G5 and transfer the wafer W to them.

In the first processing unit group G1, as shown in FIG. 2, solution treatment units each for supplying a predetermined solution to the wafer W to perform treatment, for example, resist coating units 20, 21, and 22 each for applying a resist solution to the wafer W, and bottom coating units 23 and 24 each for forming an anti-reflection film that prevents reflection of light at the time of exposure processing, are five-tiered in order from the bottom. In the second processing unit group G2, solution treatment units, for example, developing treatment units 30 to 34 each for supplying a developing solution to the wafer W to develop it are five-tiered in order from the bottom. Further, chemical chambers 40 and 41 each for supplying various kinds of treatment solutions to the solution treatment units in the processing unit groups G1 and G2 are provided on the lowermost tiers of the first processing unit group G1 and the second processing unit group G2, respectively.

As shown in FIG. 3, in the third processing unit group G3, the temperature regulating unit 60, the transition unit 61, high-precision temperature regulating units 62 to 64 each for temperature-regulating the wafer W under temperature control with a high precision and defect inspection apparatuses 110 and 110 are seven-tiered in order from the bottom. To the defect inspection apparatuses 110, a defect classification apparatus 200 is connected as shown in FIG. 1 which classifies defects of the wafer W from an inspection object image captured in the defect inspection apparatus 110.

As shown in FIG. 3, in the fourth processing unit group G4, for example, a high-precision temperature regulating unit 70, pre-baking units 71 to 74 each for performing heat processing on the wafer W after the resist coating treatment, and post-baking units 75 to 79 each for performing heat processing on the wafer W after the developing treatment, are ten-tiered in order from the bottom.

In the fifth processing unit group G5, a plurality of thermal processing units each for performing thermal processing on the wafer W, for example, high-precision temperature regulating units 80 to 83 and post-exposure baking units 84 to 89 each for performing heat processing on the wafer W after exposure are ten-tiered in order from the bottom.

A plurality of processing and treatment units are arranged, as shown in FIG. 1, on the X-direction positive direction side of the first transfer unit A1, for example, adhesion units 90 and 91 each for performing hydrophobic treatment on the wafer W and heating units 92 and 93 each for heating the wafer W being four-tiered in order from the bottom as shown in FIG. 3. As shown in FIG. 1, on the X-direction positive direction side of the second transfer unit A2, for example, an edge exposure unit 94 is disposed which selectively exposes only the edge portion of the wafer W to light.

In the interface station 4, for example, a wafer transfer body 101 moving on a transfer path 100 extending in the X-direction and a buffer cassette 102 are provided as shown in FIG. 1. The wafer transfer body 101 is movable in the Z-direction and also rotatable in the O-direction and thus can access the aligner (not shown) adjacent to the interface station 4, the buffer cassette 102, and the fifth processing unit group G5 and transfer the wafer W to them.

Next, the configurations of the above-described defect inspection apparatuses 110 and the defect classification apparatus 200 will be described.

Figure 4:
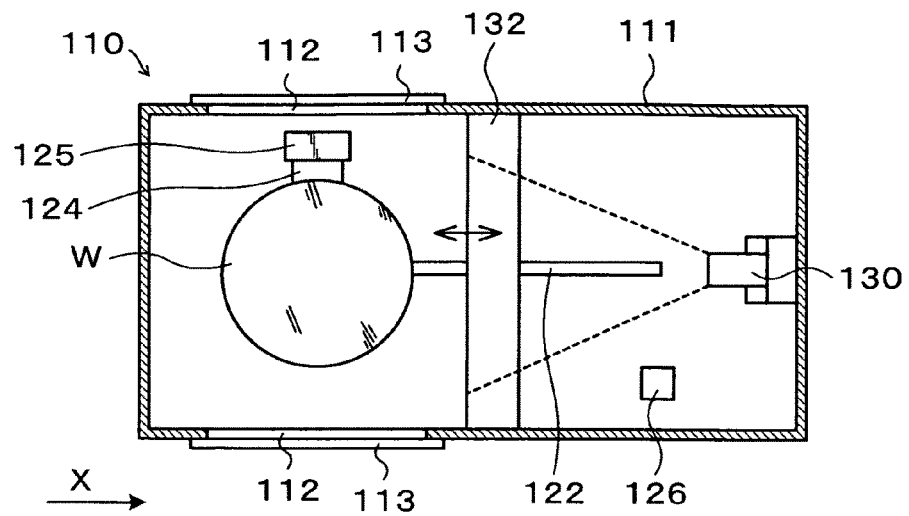
FIG. 4 A transverse sectional view schematically showing a configuration of a defect inspection apparatus.

The defect inspection apparatus 110 has a casing 111 as shown in FIG. 4. Transfer-in/out ports 112 through which the wafer W is transferred in/out are formed in both side surfaces on one end side (an X-direction negative direction side in FIG. 4) of the casing 111 and facing each other in a short side direction of the casing 111. Opening/closing shutters 113 are provided at the transfer-in/out ports 112 respectively.

Figure 5:
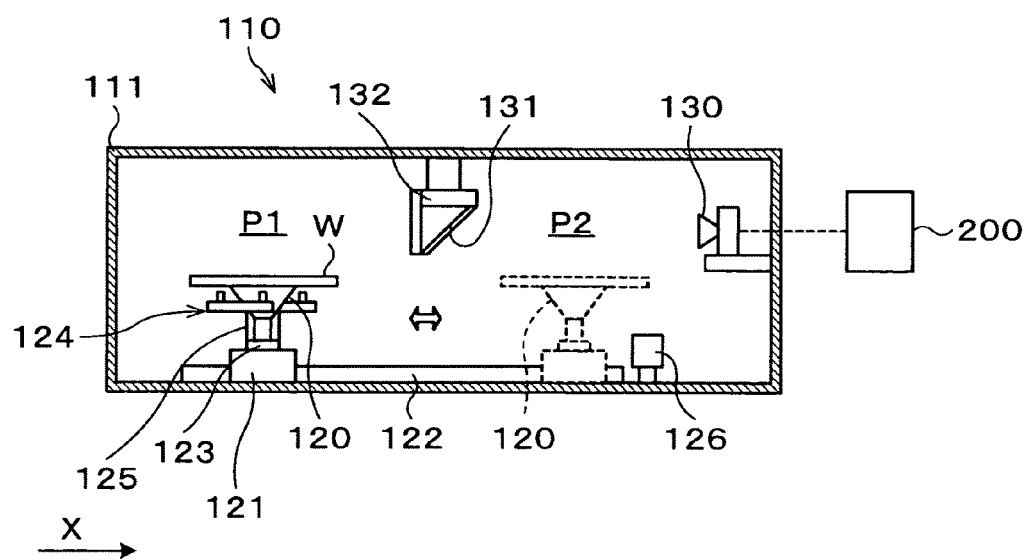
FIG. 5 A longitudinal sectional view schematically showing the configuration of the defect inspection apparatus.

In the casing 111, a mounting table 120 for mounting the wafer W thereon is provided as shown in FIG. 5. The mounting table 120 can freely rotate and stop by means of a rotation drive unit 121 such as a motor or the like and thus has an alignment function of adjusting the position of the wafer W. On the bottom surface of the casing 111, a guide rail 122 is provided which extends from one end side (an X-direction negative direction side in FIG. 5) to another end side (an X-direction positive direction side in FIG. 5). The mounting table 120 and the rotation drive unit 121 are provided on the guide rail 122 and can move along the guide rail 122 by means of a drive unit 123 such as, for example, a pulse motor.

Figure 6:
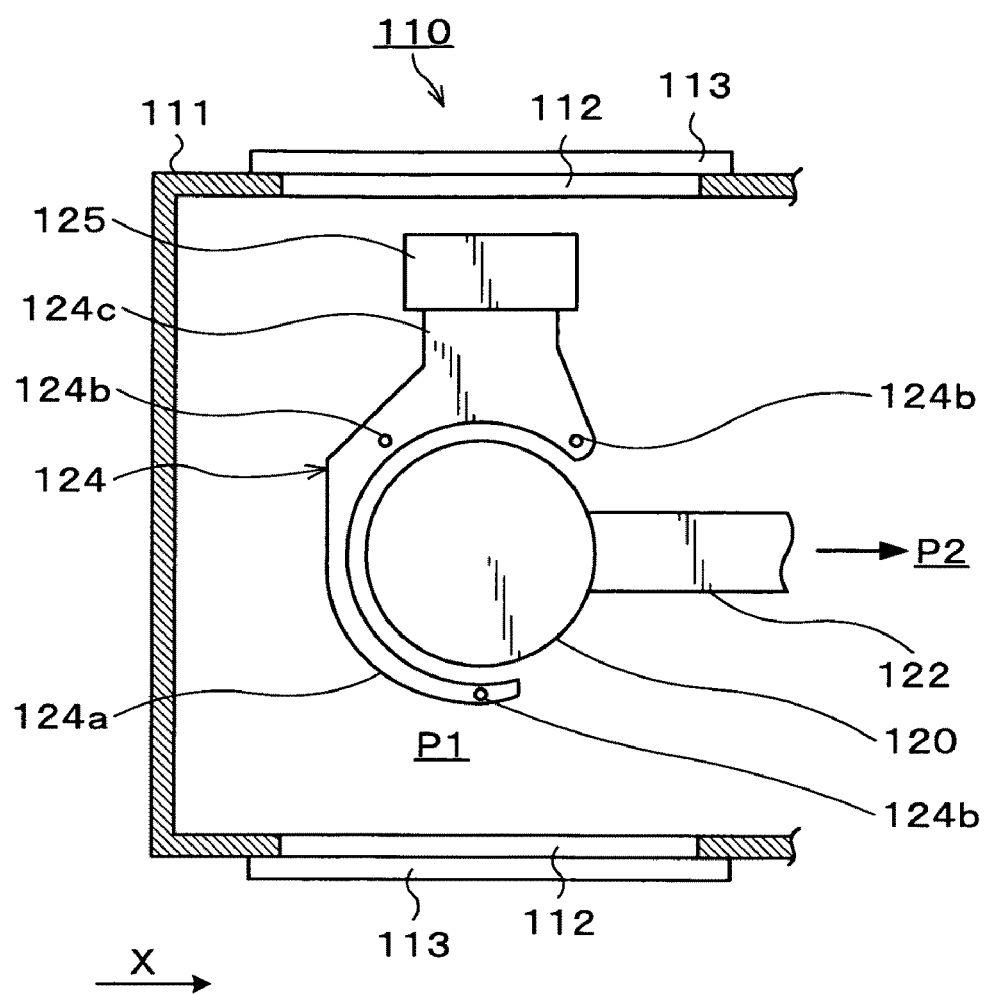
FIG. 6 A plan view schematically showing a configuration of a buffer arm.

A buffer arm 124 temporarily supporting the wafer W is provided at a position P1 (a position indicated by a solid line in FIG. 5) on the one end side in the casing 111 where the wafer W is transferred into/out of the casing 111. The buffer arm 124 has a support part 124a for the wafer W at the tip thereof as shown in FIG. 6. The support part 124a is formed, for example, in an almost ¾ circular ring shape. The diameter of the ¾ circular ring shape of the support part 124a is larger than the diameter of the mounting table 120 so that the mounting table 120 can be accommodated within the support part 124a. A cutout portion of the ¾ circular ring shape of the support part 124a is formed at the other end side (an X-direction positive direction side in FIG. 6) in the casing 111 so that the mounting table 120 can be moved to the other end side without interfering with the support part 124a. On the support part 124a, a plurality of support pins 124b are provided, and the wafer W is supported on the support pins 124b. A base part 124c of the buffer arm 124 is attached to a raising and lowering drive source 125 such as a cylinder or the like so that the buffer arm 124 can move up and down the mounting table 120.

As shown in FIG. 5, a sensor 126 for detecting the position of a notch portion of the wafer W on the mounting table 120 is provided at an alignment position P2 (a position indicated by a dotted line in FIG. 5) on the other end side in the casing 111 where the position of the notch portion of the wafer W is adjusted. The position of the notch portion of the wafer W can be adjusted by rotating the mounting table 120 by the rotation drive unit 121 while the position of the notch portion is being detected by the sensor 126.

An imaging device 130 is provided on a side surface on the other end side (the X-direction positive direction side in FIG. 5) in the casing 111. As the imaging device 130, for example, a wide-angle CCD camera is used. Near the middle of the upper portion of the casing 111, a half mirror 131 is provided. The half mirror 131 is provided at a position opposed to the imaging device 130 and inclined 45 degrees from the vertical direction. An illumination device 132 whose illuminance can be varied is provided above the half mirror 131, and the half mirror 131 and the illumination device 132 are fixed to the upper surface of the casing 111. Further, each of the imaging device 130, the half mirror 131 and the illumination device 132 is provided above the wafer W mounted on the mounting table 120. The illumination from the illumination device 132 is applied downward through the half mirror 131. Accordingly, reflection light from a body existing in an illumination region of the illumination device 132 is reflected from the half mirror 131 and taken into the imaging device 130. In other words, the imaging device 130 can capture the image of the body existing in the illumination region. Then, a captured inspection object image of the wafer W is outputted to the defect classification apparatus 200.

Figure 7:
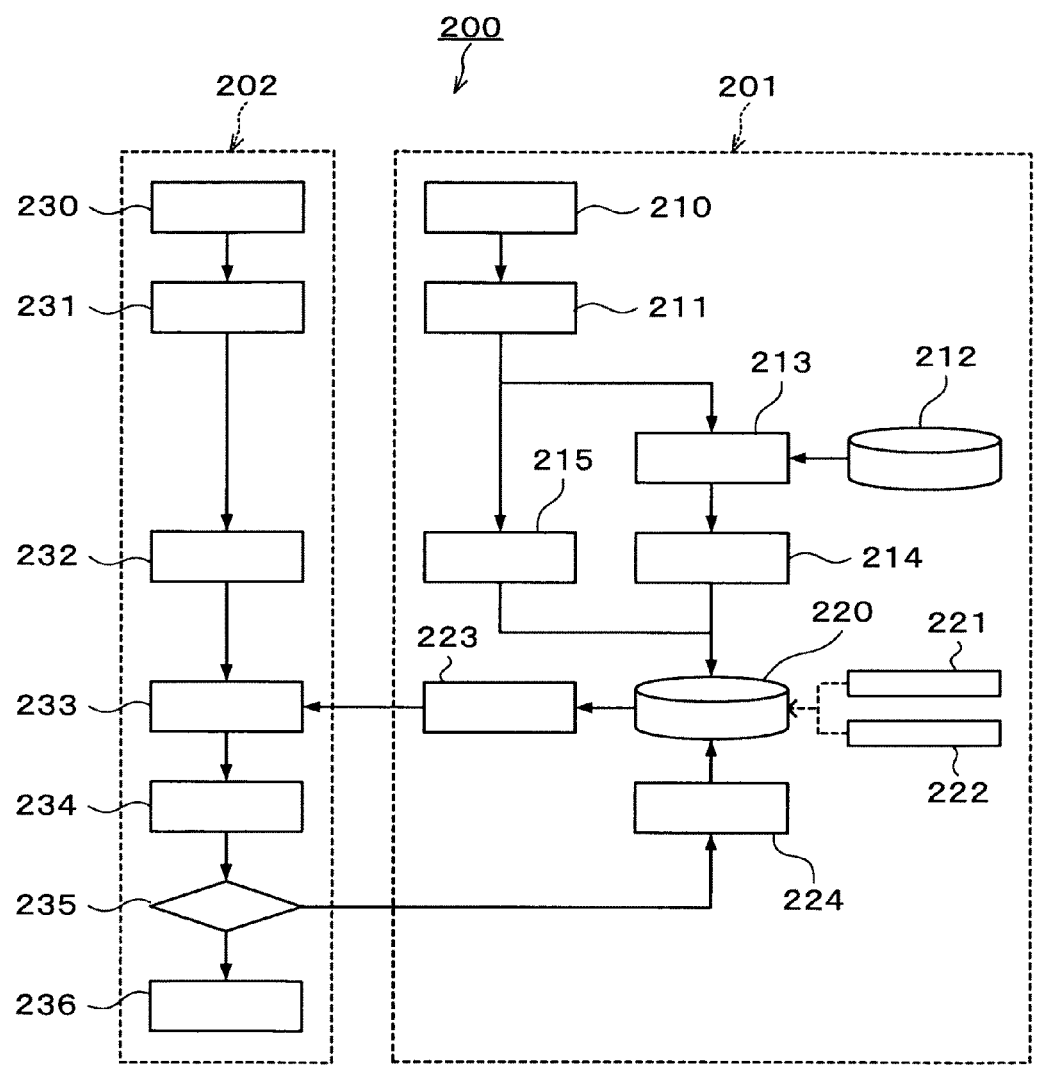
FIG. 7 A diagram schematically showing a configuration of the defect classification apparatus.

The defect classification apparatus 200 has, as shown in FIG. 7, a design unit 201 for setting classification classes of defects in advance based on the feature amounts of the defects, and a diagnosis unit 202 for classifying defects of the wafer W into the classification classes set by the design unit 201 from the inspection object image of the wafer W captured in the defect inspection apparatus 110.

The design unit 201 has a teaching image input unit 210 into which a teaching image captured in the defect inspection apparatus 110 is inputted before the inspection object image is captured. As the teaching image, one of an image of a wafer W without defect or an image of a wafer W with defect is inputted.

Figure 8:
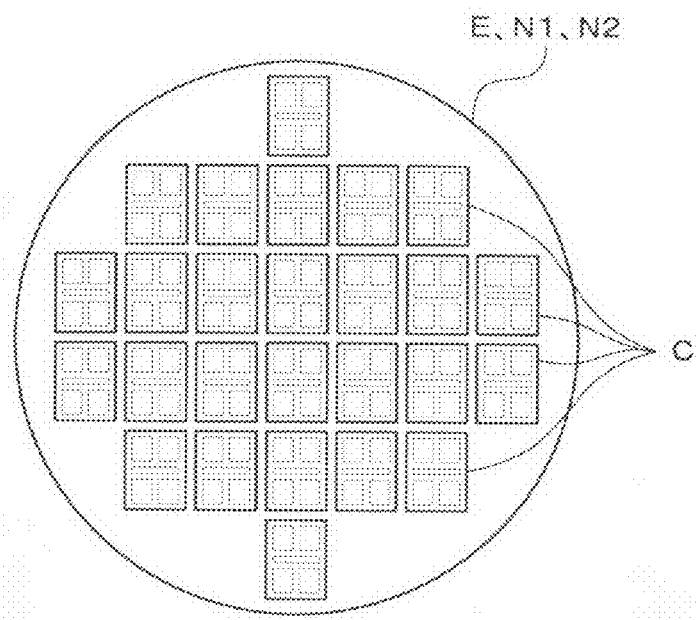
FIG. 8 An explanatory view showing inspection regions on a wafer.

The teaching image inputted into the teaching image input unit 210 is outputted to a pre-design processing unit 211. In the pre-design processing unit 211, the teaching image of the wafer W is divided into chips C as inspection regions as shown in FIG. 8. Note that the inspection regions are not limited to the regions of the chips C but can be arbitrarily set by the user.

Figure 9:
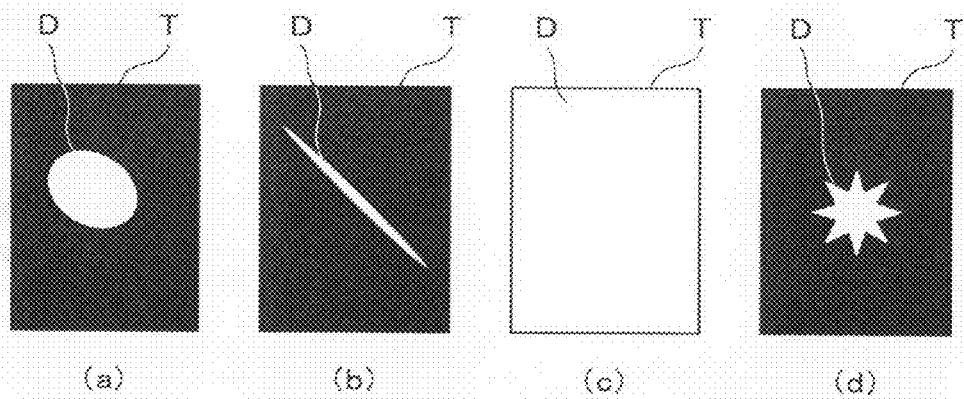
FIG. 9 Plan views exemplifying defect templates.

The design unit 201 has, as shown in FIG. 7, a template storage unit 212 for storing templates imitating defects of the wafer W (hereinafter, referred to as "defect templates"). As the defects of the defect templates, defects such as scratch, particle, hot-spot, defocus and so on are imitated in the defect templates. The defect template is created for each chip C. As shown in FIG. 9, for example, a defect template T having an almost circular defect D (FIG. 9(*a*)), a defect template T having an elongated elliptical defect D (FIG. 9(*b*)), a defect template T having a defect D existing over the entire chip C (FIG. 9(*c*)), and a defect template T having a polygonal defect D (FIG. 9(*d*)) are stored in the template storage unit 212. Defect numbers are given to these defects D and identification codes are given to the defect templates T so that they are managed in the template storage unit 212.

Figure 10:
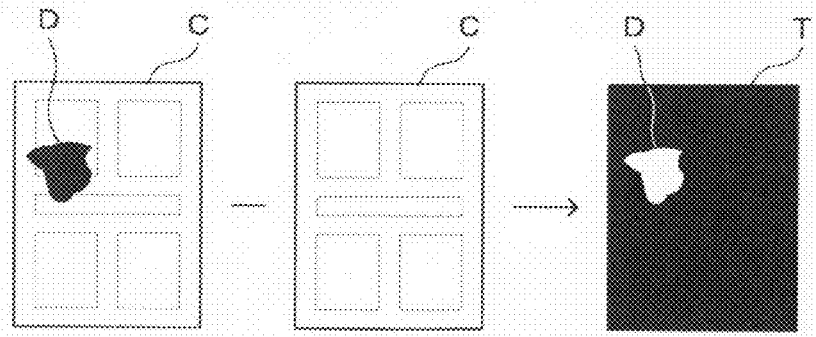
FIG. 10 An explanatory view showing the appearance of creating a defect template.

Note that as a defect template T, as shown in FIG. 10, only a defect D may be extracted from the defect image of the chip C in a wafer W obtained in another process than the process of the wafer W being the inspection object and the image of the chip C without defect, and the image of the defect D may be binarized and stored in the template storage unit 212. Further, the user can arbitrarily add defect templates T.

Figure 11:
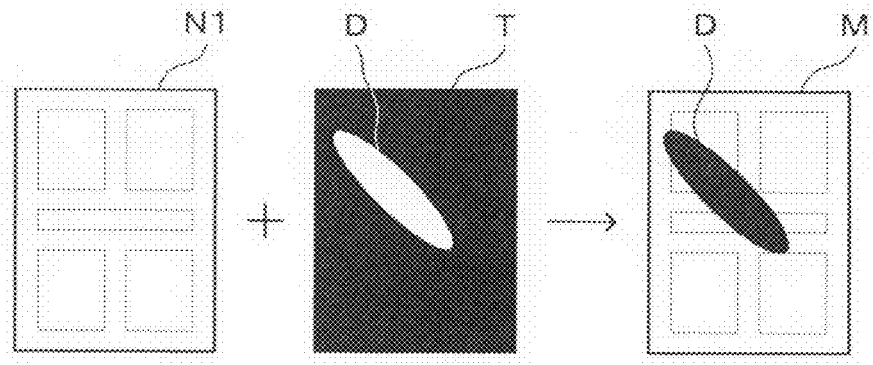
FIG. 11 Explanatory views showing the appearances of creating defect models.
Figure 11:
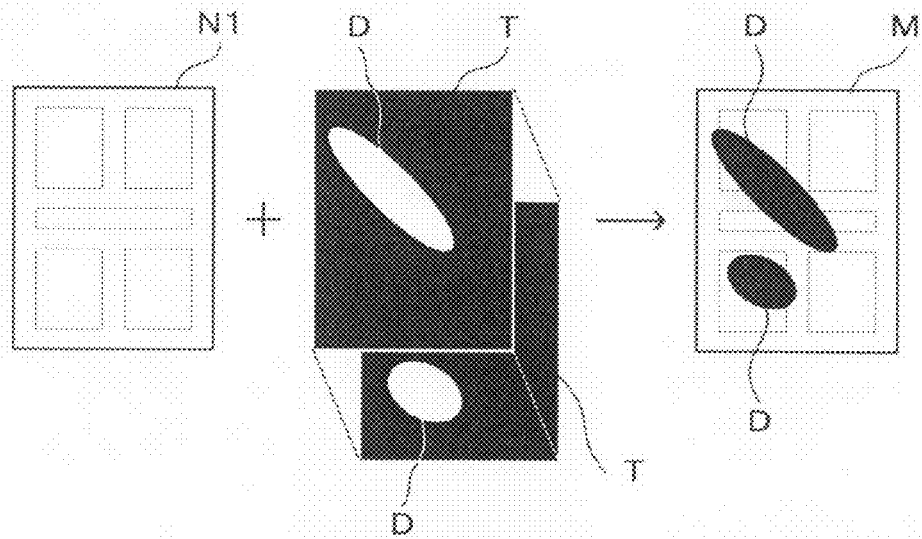

When the teaching image inputted to the teaching image input unit 210 is an image N1 of the wafer W without defect, the teaching image N1 divided in the pre-design processing unit 211 is outputted to a model creation unit 213. In the model creation unit 213, as shown in FIG. 11(*a*), the teaching image N1 and a defect template T stored in the template storage unit 212 can be combined to create a defect model M. The defect model M is created by selecting and combining the brightness of the defect template T, the size of the defect D, the position of the defect D, the angle of the defect D, the number of defects D and so on. Further, the defect model M may be created by combining the teaching image N1 and a plurality of defect templates T as shown in FIG. 11(*b*). Note that in the model creation unit 213, software GUI (Graphical User Interface) for assisting the creation of the defect model M may be provided.

The defect model M created in the model creation unit 213 is outputted as shown in FIG. 7 to a first classification class setting unit 214 for setting the classification class of the defect D in the defect model M. In the first classification class setting unit 214, the feature amounts of the defect D in the defect model M are first calculated. For example, features such as gradation, color and so on, spatial features such as texture and so on, or geometrical features such as shape features (size, shape, length, width) and so on of the defect D, are calculated as the feature amounts of the defect D. Then, a classification class of the defect D is set with respect to the calculated feature amounts of the defect D.

Besides, when the teaching image inputted to the teaching image input unit 210 is an image N2 of the wafer W with defect, the teaching image N2 divided in the pre-design processing unit 211 is outputted to a second classification class setting unit 215. In the second classification class setting unit 215, the feature amounts of the defect D in the teaching image N2 are calculated, and a classification class of the defect D is set with respect to the calculated feature amounts of the defect D.

The feature amounts and the classification classes of the defects D set in the first classification class setting unit 214 and the second classification class setting unit 215 are outputted to the storage unit 220.

Figure 12:
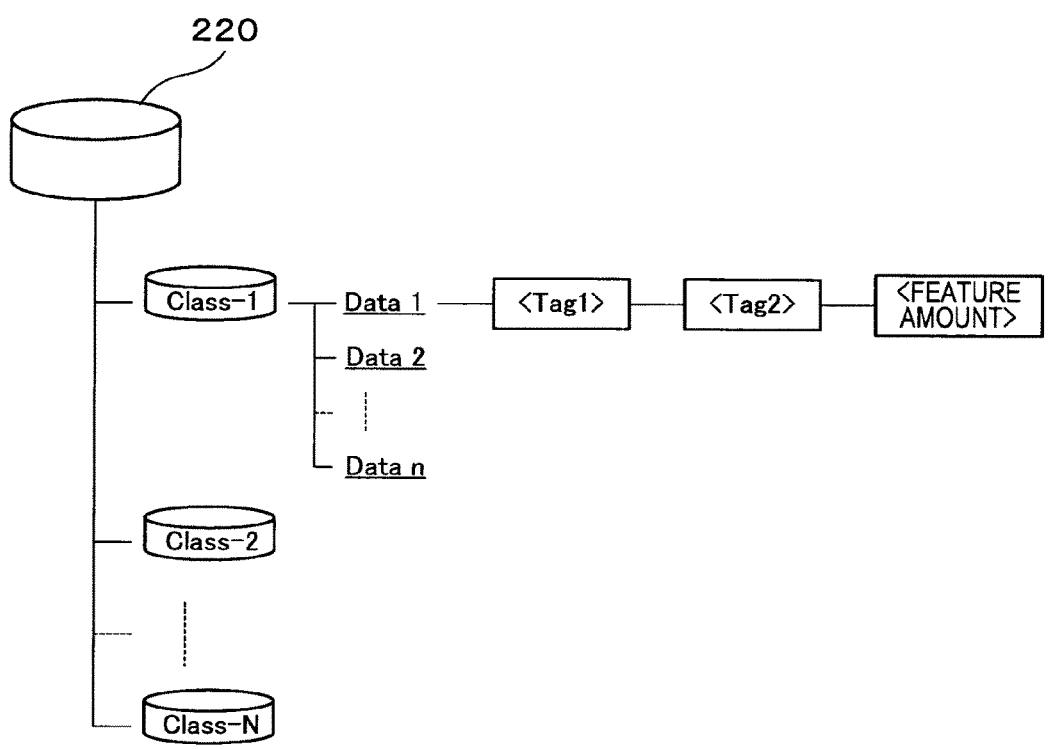
FIG. 12 An explanatory view showing data stored in a storage unit.

The feature amounts and the classification classes of the defects D outputted to the storage unit 220 are stored in the storage unit 220 such that the feature amounts and the classification classes of the defects D are linked to information (later-described Tag 1 information) and so on inherent in the wafer W as shown in FIG. 12 by a storage unit history management function 221. In the storage unit 220, management and storage are performed for each classification class of the defects (Class in FIG. 12). Further, in each classification class, the number of the defect D (Data in FIG. 12), Tag 1 information, Tag 2 information, and feature amount data of the defect D are stored in such a manner that they are linked together. As the Tag 1 information, the ID of the wafer W, the ID of the lot of the wafer W, the ID of the device in which the wafer W has been processed, the ID of the layer on the wafer W, the ID of the slot of the wafer W, the ID of the chip C, the positional information of the chip C in the wafer W, the recipe information of processing the wafer W, the processing date and time of the wafer W and so on are stored. Further, as the Tag 2 information, use/nonuse of the defect template T ("0" when used, or "1" when not used), the identification code of the defect template T, the combining conditions (the brightness of the defect template T, the angle of the defect D, the position of the defect D and so on) when creating the defect model M in the model creation unit 213, are stored. By storing accompanying information in each classification class of defects D in the linking manner as described above, the history of the accompanying data can be easily searched and extracted and the learning history stored in the storage unit 220 can be managed. Note that when a sufficient data storage region can be secured in the storage unit 220, the defect models M and the teaching images N1 and N2 can be saved. Further, a plurality of storage units 220 may be provided in the design unit 201.

Figure 13:
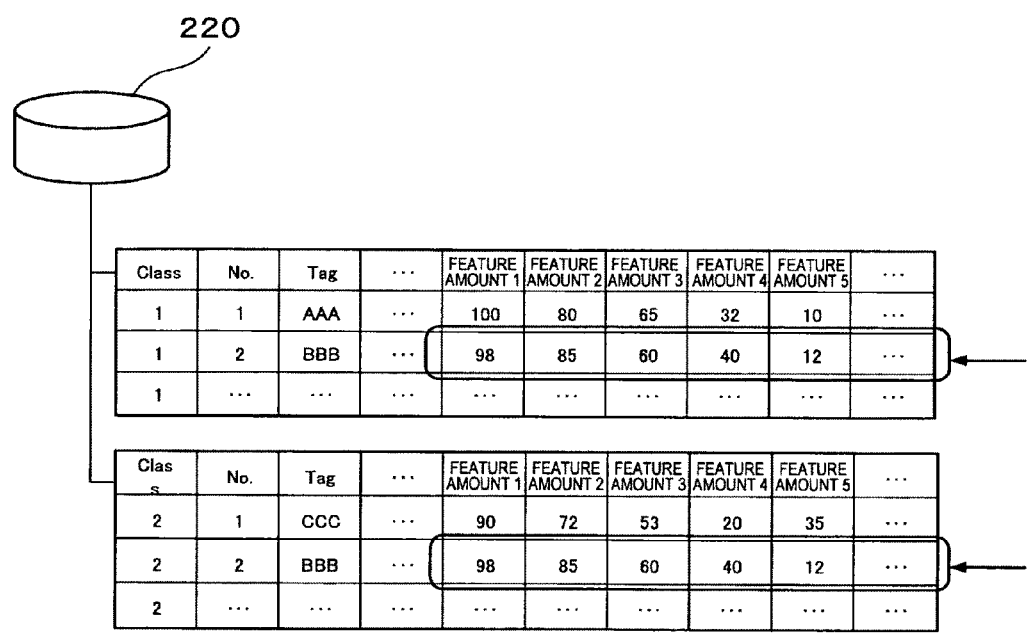
FIG. 13 An explanatory view showing a case where different classification classes with respect to the feature amounts of the same defect are set in the storage unit.

In the storage unit 220, whether or not different classification classes are stored with respect to the feature amounts of the same defect D can be checked by a storage unit check function 222 shown in FIG. 7. If different classification classes are saved with respect to the feature amounts of the same defect D as shown in FIG. 13, the user is notified of the presence of the different classification classes saved and can select deletion of one of the classification classes or deletion of both of the classification classes. This function makes it possible to store one classification class with respect to the feature amounts of one defect D, thereby properly classifying the defect D.

The diagnosis unit 202 has, as shown in FIG. 7, an inspection object image input unit 230 to which the inspection object image of the wafer W captured in the defect inspection apparatus 110 is inputted.

The inspection object image inputted to the inspection object image input unit 230 is outputted to a pre-processing unit 231. In the pre-processing unit 231, an inspection object image E of the wafer W is divided into chips C as inspection regions similarly to the dividing processing in the pre-design processing unit 211 shown in FIG. 8.

The inspection object image E divided in the pre-processing unit 231 is outputted to a feature amount calculation unit 232 as shown in FIG. 7. In the feature amount calculation unit 232, the feature amounts of a defect D for each of the chips C in the inspection object image E are calculated. As the feature amounts of the defect D, the same parameters as those of the feature amounts stored in the storage unit 220 are calculated so that, for example, features such as gradation, color and so on, spatial features such as texture and so on, or geometrical features such as shape features and so on of the defect D, are calculated as the feature amounts of the defect D.

The feature amounts of the defects D calculated in the feature amount calculation unit 232 are outputted to a classification unit 233 for classifying the defects D into classification classes. In the classification unit 233, the defects are classified into the classification classes using a learning-type classification method from the relations between the feature amounts and the classification classes of the defects D stored in the storage unit 220. As the learning-type classification method, for example, a method such as a neural network, k-NN (k-Nearest Neighbor), TFC (Test Feature Classifier) or the like is used. Note that to adapt the data in the storage unit 220 to such learning-type classification method, a learning and training unit 223 is provided in the design unit 201. In the learning and training unit 223, "selection and extraction" "optimization of weighting coefficient" "deletion of useless data" and so on of the feature amount data in the storage unit 220 are performed in consideration of, for example, the learning efficiency (calculation time and classification accuracy). Further, if there are a plurality of storage units 220, switching and selection among them are performed.

The diagnosis unit 202 has a post-processing unit 234 for bringing a plurality of classification classes into correspondence with a single classification category. In the post-processing unit 234, the defects D are classified into a classification category based on the above-described correspondence between the classification classes and the classification category, for example, when there is a problem of over-segmentation of classification classes classified in the classification unit 233. For example, for defects D in classification classes 3 to 6, the defects are classified into a classification category, Category 1.

The diagnosis unit 202 has a confirmation unit 235 in which the user can confirm when necessary whether the classification class classified in the classification unit 233 or the classification category classified in the post-processing unit 234 is adequate or not. In the confirmation unit 235, when the user judges that the classification class or the classification category of the defect D is incorrect, the feature amounts of the defect D are outputted to a classification class correction unit 224 of the design unit 201. Then, a correct classification class is set in the classification class correction unit 224, and the result of setting is outputted to the storage unit 220 and the classification class in the storage unit 220 is corrected.

Figure 14:
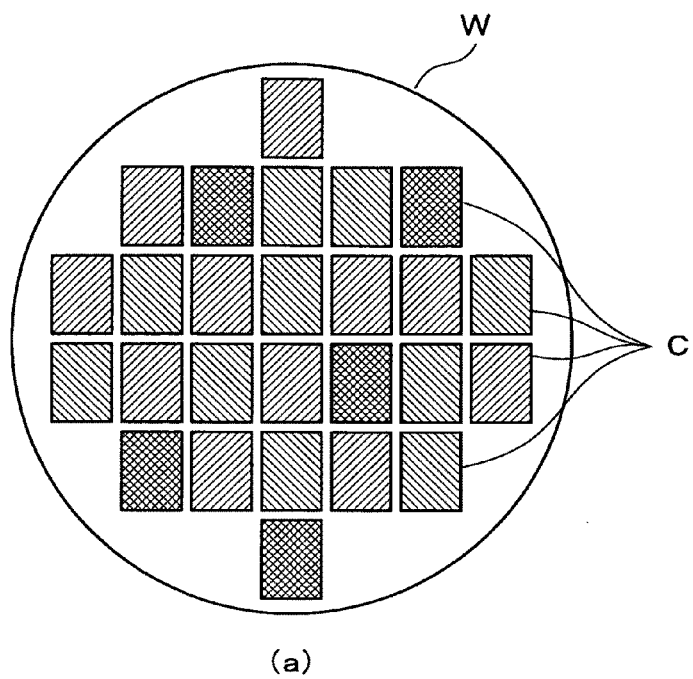
FIG. 14 Explanatory views showing classification of defects reported by a report unit.

The diagnosis unit 202 has a report unit 236 for visualizing the classified defects D on the wafer W and reporting the resulting defects D. In the report unit 236, the classification class of the defect D for each of the chips C on the wafer W is displayed as shown in FIG. 14(a), and a correspondence table between the classification class (classification result in FIG. 14(b)) and the feature amounts of the defect D as shown in FIG. 14(b).

Note that the defect classification apparatus 200 including the design unit 201 and the diagnosis unit 202 is, for example, a computer and has a program for executing the above-described defect classification of the wafer W. The aforementioned program may be the one that is stored, for example, in a computer-readable storage medium such as a hard disk (HD), a compact disk (CD), a magneto-optical disk (MO) or a memory card, and installed from the storage medium into the defect classification apparatus 200.

Next, the inspection of the wafer W for defects performed in the defect inspection apparatus 110 and the classification of the defects of the wafer W performed in the defect classification apparatus 200 configured as described above will be described together with the process of the wafer processing performed in the whole coating and developing treatment system 1.

First of all, one wafer W is taken out of the cassette C on the cassette mounting table 5 by the wafer body 7 and transferred to the temperature regulating unit 60 in the third processing unit group G3. The wafer W transferred to the temperature regulating unit 60 is temperature-regulated to a predetermined temperature, and then transferred by the first transfer arm 10 to the bottom coating unit 23, where an anti-reflection film is formed. The wafer W on which the anti-reflection film has been formed is transferred by the first transfer arm 10 to the heating unit 92 and the high-precision temperature regulating unit 70 in sequence and subjected to predetermined processing in each of the units. The wafer W is then transferred to the resist coating unit 20.

After the resist film is formed on the wafer W in the resist coating unit 20, the wafer W is transferred by the first transfer arm 10 to the pre-baking unit 71 and subsequently transferred by the second transfer arm 11 to the edge exposure unit 94 and the high-precision temperature regulating unit 83 in sequence and subjected to predetermined processing in each of the units. The wafer W is then transferred by the wafer transfer body 101 in the interface station 4 to the aligner (not shown) where a predetermined pattern is exposed on the resist film on the wafer W. The wafer W for which the exposure processing has been completed is transferred by the wafer transfer body 101 to the post-exposure baking unit 84 and subjected to predetermined processing.

After the thermal processing in the post-exposure baking unit 84 is completed, the wafer W is transferred by the second transfer arm 11 to the high-precision temperature regulating unit 81 and temperature-regulated, and then transferred to the developing treatment unit 30 where developing treatment is performed on the wafer W, whereby a pattern is formed in the resist film. The wafer W is then transferred by the second transfer arm 11 to the post-baking unit 75 and subjected to heat-processing, and then transferred to the high-precision temperature regulating unit 63 and temperature-regulated.

The wafer W is then transferred by the first transfer arm 10 to the defect inspection apparatus 110 and subjected to defect inspection of the wafer W. Details of the defect inspection will be described later. The wafer W is then transferred by the first transfer arm 10 to the transition unit 61 and then returned by the wafer transfer body 7 to the cassette C, with which a series of photolithography process ends.

Next, the inspection method of the wafer W for defects in the defect inspection apparatus 110 and the classification method of the defects of the wafer W in the defect classification apparatus 200 will be described.

The wafer W transferred by the first transfer arm 10 into the casing 111 is mounted on the mounting table 120. When the wafer W passes under the half mirror 131 while the mounting table 120 is moved to the imaging device 130 side, illumination with a predetermined illuminance is applied to the wafer W from the illumination device 132. While illumination is being applied to the wafer W as described above, an image of the wafer W is captured by the imaging device 130. The captured inspection object image E of the wafer W is outputted to the inspection object image input unit 230 of the defect classification apparatus 200. Note that the wafer W whose inspection object image E has been captured is moved to the transfer-in/out ports 112 side and then delivered from the buffer arm 124 to the wafer transfer body 7, and transferred out of the defect inspection apparatus 110 by the transfer body 7.

The inspection object image E of the wafer W inputted to the inspection object image input unit 230 is outputted to the pre-processing unit 231 and divided into chips C. The divided inspection object image E is outputted to the feature amount calculation unit 232 and the feature amounts of defects D are calculated from the inspection object image E.

The feature amounts of the defects D in the inspection object image E calculated in the feature amount calculation unit 232 are outputted to the classification unit 233. The classification unit 233 classifies the defects using the learning-type classification method. In this embodiment, the case using the k-NN (k-Nearest Neighbor) method as the learning-type classification method will be described. This k-NN method is the method of comparing the feature amounts of the defect D inputted from the feature amount calculation unit 232 with the feature amount data of the defects D previously stored in the storage unit 220 on a feature amount space and outputting the classification class that the most analogous (nearest in distance) feature amount data, namely, the nearest-neighbor feature amount data belongs to. In other words, by increasing the nearest-neighbor definition (k-value), a more suitable classification class from a frequency distribution of classification classes that upper k pieces of the analogous feature amount data belong to is outputted.

Concretely describing the classification method in the classification unit 233, the sum of squares of deviation (distance) of the feature amounts of the defect D from the feature amount calculation unit 232 and every piece of feature amount data in the storage unit 220 is calculated first. Then, the calculated distance data are sorted in ascending order. Upper k pieces of the sorted distance data are extracted. A most frequent classification class is found in the frequency distribution of the extracted data. Then, the classification class is outputted as the classification result of the defect D.

When the classification classes classified in the classification unit 233 are the classification classes that can be used as they are for all of the chips C of the wafer W, the classification classes are outputted to the report unit 236. In the report unit 236, the classification class of the defect D for each of the chips C on the wafer W is displayed as shown in FIG. 14(a), and the correspondence table between the classification class and the feature amounts of the defect D is displayed as shown in FIG. 14(b).

On the other hand, when there is a problem of over-segmentation of classification classes classified in the classification unit 233, the defects D are classified in the post-processing unit 234 into a classification category based on the above-described correspondence between the classification classes and the classification category. For example, for defects D in the classification classes 3 to 6, the defects D are classified into the classification category, Category 1. The classification category is then outputted to the report unit 236, and the classification category for each of the chips C is visualized on the wafer W.

Note that in the confirmation unit 235, the user can confirm when necessary whether the classification class classified in the classification unit 233 or the classification category classified in the post-processing unit 234 is adequate or not. In the confirmation unit 235, when the user judges that the classification class or the classification category of the defect D is incorrect, the feature amounts of the defect D are outputted to the classification class correction unit 224 of the design unit 201. Then, a correct classification class is set in the classification class correction unit 224, and the result of setting is outputted to the storage unit 220. Thus, the classification class in the storage unit 220 is corrected.

According to the above embodiment, the defect templates T are created in advance and stored in the template storage unit 212, and the defect templates T and the teaching image N1 without defect are combined to create the defect models M in the model creation unit 213, so that the defect models M can be used as the defect images in the conventional learning-type classification method. Then, the feature amounts of the defect D in the defect model M are calculated and a classification class of the defect D is set with respect to the feature amounts of the defect D in the first classification class setting unit 214, and the relation between the feature amounts of the defect D and the classification class of the defect D can be stored in the storage unit 220. Accordingly, even when there is no defect image or there are a small number of defect images, defects D of the wafer W can be properly classified from the feature amounts of the defects D of the wafer W calculated in the feature amount calculation unit 232 using the relations between the feature amounts of the defects D and the classification classes of the defects D stored in the storage unit 220.

Further, since the image inputted to the teaching image input unit 210 is divided into chips C as inspection regions in the pre-design processing unit 211, the defects D of the wafer W can be further segmented and properly classified.

Since the feature amounts and the classification classes of the defects D are linked by the storage unit history management function 221 to information (the above-described Tag 1 information) and so on inherent in the wafer W in the storage unit 220, the information of the wafer W can be easily searched and extracted from the classification classes, and the learning history stored in the storage unit 220 can be managed.

Further, in the storage unit 220, whether or not different classification classes are stored with respect to the feature amounts of the same defect D can be checked by the storage unit check function 222. If the defect D is set in different classification classes with respect to the feature amounts of the same defect D, one of the classification classes can be deleted or both of the classification classes can be deleted. Therefore, one classification class with respect to the feature amounts of one defect D can be stored in the storage unit 220 so that the defect D can be properly classified.

When the teaching image inputted to the teaching image input unit 210 is the image N1 of the wafer W with defect, the feature amounts of the defect D in the teaching image N1 are calculated and a classification class of the defect D is set with respect to the calculated feature amounts of the defect D in the second classification class setting unit 215. Therefore, the relation between the feature amounts and the classification class of the defect D can be further stored in the storage unit 220. This can increase the relation between the feature amounts and the classification class of the defect D stored in the storage unit 220 and improve the accuracy of the relation because actual defect data is inputted.

Further, the post-processing unit 234 brings a plurality of classification classes into correspondence with a single classification category and therefore can classify the defects D into proper classification categories, for example, even when there is a problem of over-segmentation of classification classes classified in the classification unit 233.

Further, since the user can confirm when necessary in the confirmation unit 235 whether the classification class classified in the classification unit 233 or the classification category classified in the post-processing unit 234 is adequate or not, incorrect classification of the defect D can be prevented. Further, when it is judged that the classification class or the classification category is incorrect, the classification class with respect to the feature amounts of the defect D is corrected in the classification class correction unit 224, so that the accuracy of the classification class in the storage unit 220 can be further improved.

Figure 15:
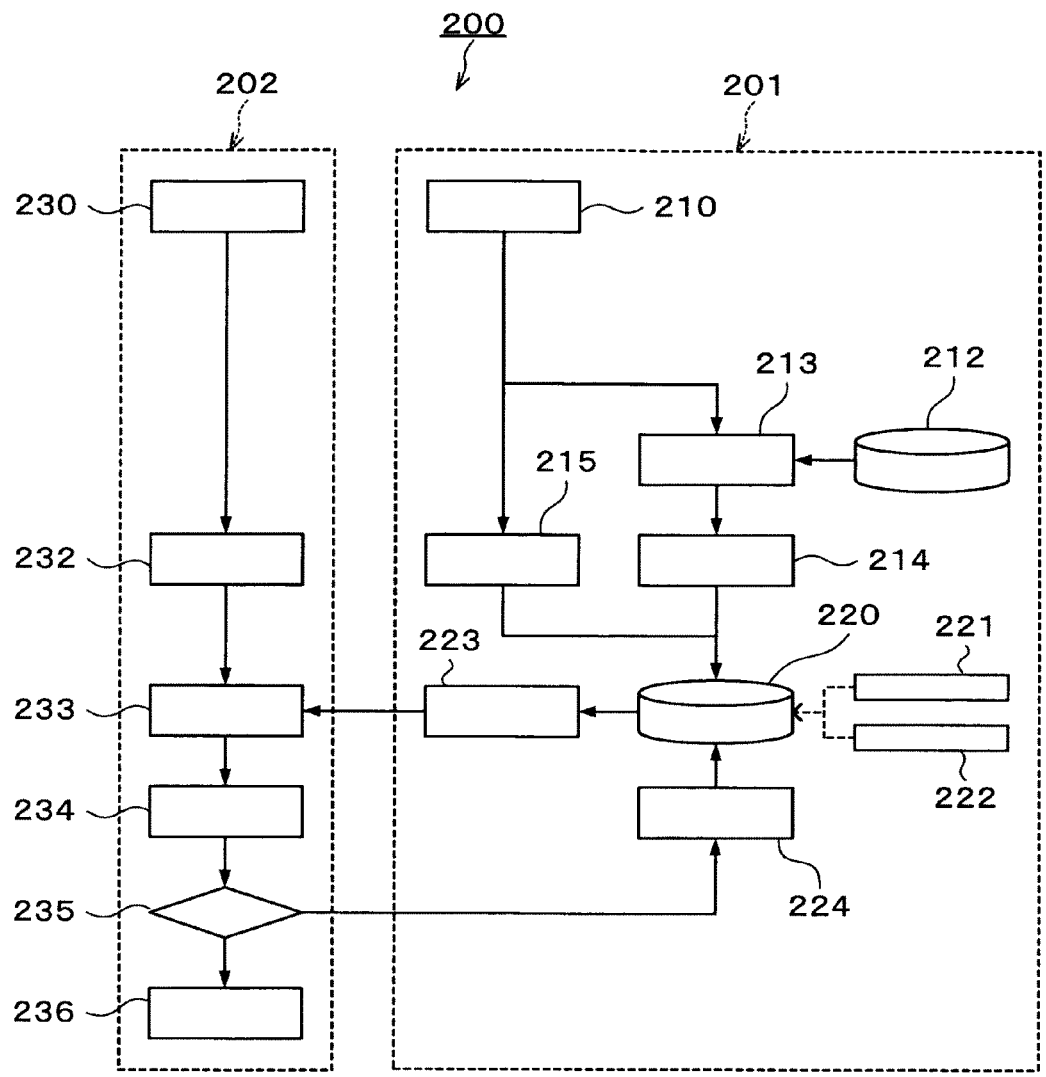
FIG. 15 A diagram schematically showing a configuration of a defect classification apparatus in another embodiment.
Figure 16:
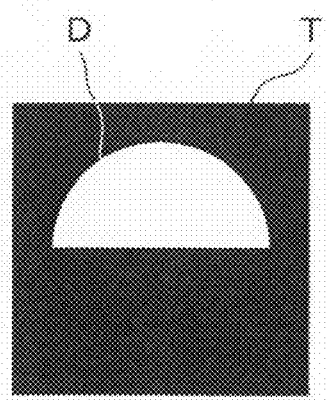
FIG. 16 Plan views exemplifying defect templates of the entire wafer.
Figure 16:
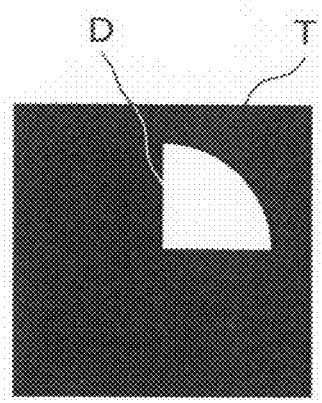
Figure 16:
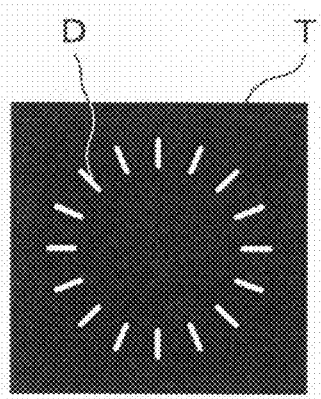
Figure 16:
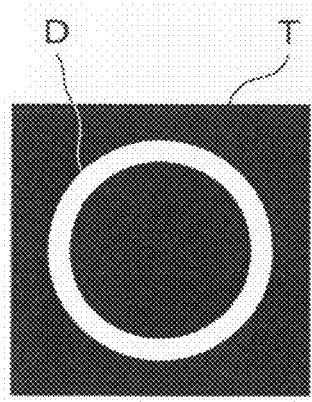

Though each of the teaching images N1 and N2 inputted to the teaching image input unit 210 and the inspection object image E inputted to the inspection object image input unit 230 is divided into chips C in the above embodiment, the defects D on the entire wafer W may be classified without dividing the teaching images N1 and N2 and the inspection object image E. In this case, the dividing processing in the pre-design processing unit 211 and the pre-processing unit 231 can be omitted as shown in FIG. 15. As the defect templates T to be stored in the template storage unit 212, for example, as shown in FIG. 16, a defect template T having a defect in an upper half of the wafer W (FIG. 16(a)), a defect template T having a defect in an quarter of the wafer W (FIG. 16(b)), a defect template T having a defect in a ring shape at a peripheral portion of the wafer W (FIG. 16(d)), and a defect template T having a plurality of defects at regular intervals at a peripheral portion of an upper half of the wafer W (FIG. 16(c)) and so on are used. In this case, the defects D on the entire wafer W can be classified by a method similar to the above-described defect classification method.

Preferred embodiments of the present invention have been described above with reference to the accompanying drawings, but the present invention is not limited to the embodiments. It should be understood that various changes and modifications are readily apparent to those skilled in the art within the scope of the spirit as set forth in claims, and those should also be covered by the technical scope of the present invention. The present invention is not limited to the embodiments but can take various forms. The present invention is also applicable to the case where the substrate is a substrate other than the wafer, such as an FPD (Flat Panel Display), a mask reticle for a photomask, or the like.

INDUSTRIAL APPLICABILITY

The present invention is useful in classifying defects of a substrate based on a captured image of the substrate.

What is claimed:

1. A defect classification method of classifying defects of a substrate based on a captured inspection object image of the substrate, comprising:
   a design step of setting classification classes of defects based on feature amounts of the defects and storing relations between the feature amounts of the defects and the classification classes into a storage unit;
   a feature amount calculation step of calculating the feature amounts of the defects of the substrate from the captured inspection object image of the substrate; and
   a classification step of classifying the defects of the substrate into the classification classes from the relations between the feature amounts of the defects and the classification classes stored in the storage unit based on the calculated feature amounts of the defects,
   said design step comprising:
   a first step of creating a plurality of defect templates;
   a second step of combining a teaching image of a substrate without defect with the defect template to create a defect model;
   a third step of calculating feature amounts of a defect in the defect model;
   a fourth step of setting a classification class of the defect with respect to the feature amounts of the defect in the defect model; and
   a fifth step of storing a relation between the feature amounts of the defect and the classification class into the storage unit.

2. The defect classification method as set forth in claim 1, wherein in said second step, the teaching image of the substrate without defect is combined with a plurality of the defect templates to create the defect model.

3. The defect classification method as set forth in claim 1, wherein in said design step, the feature amounts of the defects and the classification classes in the storage unit are linked to information inherent in the substrate.

4. The defect classification method as set forth in claim 1, wherein in said design step, when the defect is set in different classification classes with respect to the feature amounts of the same defect, one of the classification class is deleted or both of the classification classes are deleted.

5. The defect classification method as set forth in claim 1, wherein in said design step, when there is a teaching image of a substrate with defect,
   feature amounts of a defect are calculated from the teaching image,
   a classification class of the defect is set with respect to the feature amounts of the defect in the teaching image, and
   a relation between the feature amounts of the defect and the classification class is further stored into the storage unit.

6. The defect classification method as set forth in claim 1, wherein the substrate is divided into a plurality of inspection regions,
   wherein in said feature amount calculation step, feature amounts of defects in the inspection regions are calculated, and
   wherein in said classification step, the inspection regions are classified into the classification classes.

7. The defect classification method as set forth in claim 1, wherein after said classification step, when the classification class of the defect of the substrate is confirmed and the classification class is judged to be incorrect, the relation between the feature amounts of the defect and the classification class in the storage unit is corrected.

8. The defect classification method as set forth in claim 1, wherein after said classification step, based on a predetermined relation between a plurality of classification classes and a single classification category, the defects of the substrate are classified into the classification category.

9. A computer-readable storage medium storing a program running on a computer of a defect classification apparatus to cause the defect classification apparatus to execute a defect classification method of classifying defects of a substrate based on a captured inspection object image of the substrate, said defect inspection method, comprising:
- a design step of setting classification classes of defects based on feature amounts of the defects and storing relations between the feature amounts of the defects and the classification classes into a storage unit;
- a feature amount calculation step of calculating the feature amounts of the defects of the substrate from the captured inspection object image of the substrate; and
- a classification step of classifying the defects of the substrate into the classification classes from the relations between the feature amounts of the defects and the classification classes stored in the storage unit based on the calculated feature amounts of the defects, said design step comprising:
- a first step of creating a plurality of defect templates;
- a second step of combining a teaching image of a substrate without defect with the defect template to create a defect model;
- a third step of calculating feature amounts of a defect in the defect model;
- a fourth step of setting a classification class of the defect with respect to the feature amounts of the defect in the defect model; and
- a fifth step of storing a relation between the feature amounts of the defect and the classification class into the storage unit.

10. A defect classification apparatus for classifying defects of a substrate based on a captured inspection object image of the substrate, comprising:
- a design unit for setting classification classes of defects based on feature amounts of the defects; and
- a diagnosis unit for classifying the defects of the substrate into the classification classes set by said design unit from the captured inspection object image of the substrate, said design unit comprising:
- a template storage unit storing a plurality of defect templates;
- a model creation unit for combining a teaching image of a substrate without defect with the defect template to create a defect model;
- a classification class setting unit for calculating feature amounts of a defect in the defect model and setting a classification class of the defect with respect to the feature amounts of the defect; and
- a storage unit for storing a relation between the feature amounts of the defect and the classification class, said diagnosis unit comprising:
- a feature amount calculation unit for calculating the feature amounts of the defects of the substrate from the captured inspection object image of the substrate; and
- a classification unit for classifying the defects of the substrate into the classification classes from the relations between the feature amounts of the defects and the classification classes stored in said storage unit based on the calculated feature amounts of the defects.

11. The defect classification apparatus as set forth in claim 10, wherein said model creation unit combines the teaching image of the substrate without defect with a plurality of the defect templates to create the defect model.

12. The defect classification apparatus as set forth in claim 10, wherein said design unit has a storage unit history management function of storing data of the feature amounts and the classification classes in said storage unit while linking the feature amount data and the classification classes to information inherent in the substrate.

13. The defect classification apparatus as set forth in claim 10, wherein said design unit has a storage unit check function of deleting, when the defect is set in different classification classes with respect to the feature amounts of the same defect in said storage unit, one of the classification class or both of the classification classes.

14. The defect classification apparatus as set forth in claim 10, wherein said design unit has another classification class setting unit for calculating feature amounts of a defect from a teaching image of a substrate with defect and setting a classification class of the defect with respect to the feature amounts of the defect, and wherein a relation between the feature amounts of the defect and the classification class is stored into said storage unit.

15. The defect classification apparatus as set forth in claim 10, wherein said diagnosis unit has a pre-processing unit for dividing the substrate into a plurality of inspection regions, wherein said feature amount calculation unit calculates feature amounts of defects in the inspection regions, and wherein said classification unit classifies the inspection regions into the classification classes.

16. The defect classification apparatus as set forth in claim 10, wherein said diagnosis unit has a confirmation unit for confirming the classification class of the defect of the substrate classified in said classification unit, and wherein when said confirmation unit judges that the classification class is incorrect, the relation between the feature amounts of the defect and the classification class in said storage unit is corrected.

17. The defect classification apparatus as set forth in claim 10, wherein said diagnosis unit has a post-processing unit for bringing a plurality of classification classes into correspondence with a single classification category, and wherein said post-processing unit classifies the defects of the substrate into a plurality of classification categories based on the correspondence.

* * * * *